US009867524B2

(12) United States Patent
Jono et al.

(10) Patent No.: US 9,867,524 B2
(45) Date of Patent: Jan. 16, 2018

(54) OPTICAL FIBER ASSEMBLY, METHOD OF FABRICATING SAME, AND PROBE

(71) Applicant: KONICA MINOLTA, INC., Chiyoda-ku (JP)

(72) Inventors: Junichi Jono, Kita-ku (JP); Kikuo Iwasaka, Iruma-gun (JP)

(73) Assignee: KONICA MINOLTA, INC., Tokyo (JP)

( * ) Notice: Subject to any disclaimer, the term of this patent is extended or adjusted under 35 U.S.C. 154(b) by 482 days.

(21) Appl. No.: 14/411,821

(22) PCT Filed: Jun. 21, 2013

(86) PCT No.: PCT/JP2013/067044
§ 371 (c)(1),
(2) Date: Dec. 29, 2014

(87) PCT Pub. No.: WO2014/002882
PCT Pub. Date: Jan. 3, 2014

(65) Prior Publication Data
US 2015/0148689 A1    May 28, 2015

(30) Foreign Application Priority Data

Jun. 27, 2012    (JP) .................................. 2012-143992

(51) Int. Cl.
*A61B 6/00*    (2006.01)
*A61B 1/00*    (2006.01)
(Continued)

(52) U.S. Cl.
CPC ...... *A61B 1/00167* (2013.01); *A61B 1/00096* (2013.01); *A61B 1/0125* (2013.01);
(Continued)

(58) Field of Classification Search
CPC ............ A61B 1/00167; A61B 1/00163; A61B 1/00165; A61B 1/07; A61B 1/0125;
(Continued)

(56) References Cited

FOREIGN PATENT DOCUMENTS

JP    2007-132792    5/2007
JP    2011-72424    4/2011
(Continued)

OTHER PUBLICATIONS

Jono et al , WIPO Publication No. WO 2010/137375 A1. Machine translation.*

*Primary Examiner* — Mallika D Fairchild
(74) *Attorney, Agent, or Firm* — Cozen O'Connor

(57) ABSTRACT

An optical fiber assembly includes optical fibers, an array member, an adhesive part, a cylindrical member and a fixing member. The fibers are inserted into the array member, and the array member is inserted into a cylindrical part of the cylindrical member. The adhesive part is disposed on one-end side of the array member. The fibers extend through the one end. The cylindrical part and the fixing member are fixed to each other in a state in which (i) the array member is sandwiched between a terminal part of the cylindrical member and the fixing member in an axial direction and (ii) the array member is positioned in the axial direction in relation to the cylindrical part. Thereby, the array member and the adhesive part are housed in a structure constituted of the cylindrical member and the fixing member.

6 Claims, 6 Drawing Sheets

(51) Int. Cl.

| | |
|---|---|
| *G02B 6/36* | (2006.01) |
| *A61B 1/012* | (2006.01) |
| *A61B 1/04* | (2006.01) |
| *B32B 37/12* | (2006.01) |
| *B32B 37/14* | (2006.01) |
| *G02B 6/32* | (2006.01) |
| *A61B 1/07* | (2006.01) |
| *G02B 6/26* | (2006.01) |
| *A61B 5/00* | (2006.01) |

(52) U.S. Cl.
CPC ............... *A61B 1/043* (2013.01); *A61B 1/07* (2013.01); *B32B 37/1292* (2013.01); *B32B 37/142* (2013.01); *G02B 6/262* (2013.01); *G02B 6/32* (2013.01); *G02B 6/3624* (2013.01); *A61B 5/0071* (2013.01)

(58) Field of Classification Search
CPC ..... A61B 1/0017; A61B 1/043; A61B 1/0096; A61B 5/0071; A61B 2090/306; G02B 6/36; G02B 6/262; G02B 6/3624
See application file for complete search history.

(56) References Cited

FOREIGN PATENT DOCUMENTS

| JP | 2011-99963 | | 5/2011 |
|---|---|---|---|
| WO | WO2010/137375 | * | 2/2010 |

\* cited by examiner

OPTICAL FIBER ASSEMBLY, METHOD OF FABRICATING SAME, AND PROBE

RELATED APPLICATIONS

The present U.S. patent application is a U.S. National Phase Application under 35 USC 371 of International Application No. PCT/JP2013/067044 filed on Jun. 21, 2013. This application claims a priority under the Pads Convention of Japanese patent application No. 2012-143992 filed Jun. 27, 2012 the entirety of which is incorporated by references.

TECHNICAL FIELD

The present invention relates to an optical fiber assembly, a method of fabricating the same and a probe using the optical fiber assembly.

BACKGROUND ART

There is a fluorescence analysis device which irradiates an examination target with excitation light and measures fluorescent generated by the excitation light so as to analyze the examination target. In this sort of fluorescence analysis device, a probe which transmits light between the main body of the device and an examination target is used in general. In the probe, a plurality of optical fibers lie to transmit excitation light and fluorescence, respectively, and the front ends of these optical fibers are arranged and fixed on the front end side of the optical probe. (Refer to, for example, Patent Document 1.)

RELATED ART DOCUMENTS

Patent Documents

Patent Document 1: Japanese Patent Application Laid-Open Publication No. 2007-132792

SUMMARY OF THE INVENTION

Problems to be Solved by the Invention

A probe is used by being curved, and hence a plurality of optical fibers built therein are required to have predetermined levels of flexibility and strength. Therefore the lengths in the longitudinal direction of built-in components, such as an array member, which constitute a hard part are desired to be as short as possible. However, the shorter the components are, the more difficult positioning and fixation thereof in assembling are.

In the process of fabricating a probe, the front-end parts of optical fibers are arranged close to each other with an array member and made to adhere to each other with an adhesive. However, if the adhesive has high liquidity when the optical fibers are close to each other, the adhesive occasionally runs in the longitudinal direction of the optical fibers by capillary phenomenon and then spreads over a long area and solidifies therein. In the area where the adhesive solidifies, flexibility of the optical fibers decreases. Hence there is a possibility that the optical fibers are damaged when this part is curved.

Hence objects of the present invention are to prevent optical fibers from being damaged, which occurs at an adhesive part which makes an array member and optical fibers adhere to each other, and further, to make a hard part of a front-end part of a probe short, the hard part where flexibility is lost.

Means for Solving the Problems

In order to solve the above problems, the invention of claim 1 is an optical fiber assembly including: a plurality of optical fibers; an array member into which the optical fibers are inserted and which retains the optical fibers with a predetermined arrangement; an adhesive part which (i) is disposed on a one-end side where one end of the array member is disposed, the one end through which the optical fibers extend, (ii) is formed of an adhesive having curability and (iii) makes the array member and the optical fibers adhere to each other; a cylindrical member including: a cylindrical part into which the array member is inserted and which retains an outer circumference of the array member; and a terminal part which contacts another end of the array member; and a fixing member which (i) is disposed on the one-end side of the array member, (ii) is entirely or partly inserted into the cylindrical part and (iii) contacts the one end of the array member, wherein the cylindrical part and the fixing member are fixed to each other in a state in which (i) the array member is sandwiched between the terminal part and the fixing member in an axial direction and (ii) the array member is positioned in the axial direction in relation to the cylindrical part, whereby the array member and the adhesive part are housed in a structure constituted of the cylindrical member and the fixing member.

The invention of claim 2 is the optical fiber assembly according to claim 1, wherein the cylindrical member is constituted of the terminal part and the cylindrical part which are individual components.

The invention of claim 3 is the optical fiber assembly according to claim 1, wherein the cylindrical member is constituted of the terminal part and the cylindrical part which are integrated as a component.

The invention of claim 4 is the optical fiber assembly according to claim 1, 2 or 3, wherein the fixing member is provided with a retaining hole into which the optical fibers are inserted, the retaining hole is disposed a space away from the one end of the array member, the space where the adhesive part is disposed, and the optical fibers are firmly attached to each other and retained in the retaining hole.

The invention of claim 5 is a method of fabricating the optical fiber assembly according to claim 4, the method including: inserting the optical fibers into the array member; applying the adhesive which forms the adhesive part to the one-end side where the one end of the array member is disposed, the one end through which the optical fibers extend; inserting the array member into the cylindrical part; and inserting the optical fibers which extend through the one end of the array member into the retaining hole; and thereafter, inserting the fixing member into the cylindrical part in such a way as to sandwich the array member between the terminal part and the fixing member in the axial direction, thereby positioning the array member in the axial direction in relation to the cylindrical part; and curing the adhesive in a state in which the optical fibers are firmly attached to each other and retained in the retaining hole.

The invention of claim 6 is a probe including: the optical fiber assembly according to any one of claims 1 to 4; a tube into which the optical fiber assembly is inserted; and an optical connector which is disposed on one end of the tube and connects the optical fibers to an optical device, wherein the cylindrical member is fixed to another end of the tube.

Advantageous Effects of the Invention

According to the present invention, the array member and the adhesive part are housed in the structure constituted of the cylindrical member and the fixing member. Therefore the optical fibers can be prevented from being damaged, which occurs at the adhesive part which makes the array member and the optical fibers adhere to each other.

According to the fabricating method of claim 5, the adhesive is cured in the state in which the optical fibers are firmly attached to each other and retained, whereby the space between the optical fibers disappears. Therefore the adhesive can be prevented from running in the longitudinal direction of the optical fibers by capillary phenomenon and spreading over a long area and solidifying therein, and also the hard part of the front-end part of the probe, the hard part where flexibility is lost, can be made short.

EMBODIMENTS FOR CARRYING OUT THE INVENTION

Hereinafter, embodiments of the present invention are described with reference to the drawings. The followings are not limitations to but embodiments of the present invention.

Figure 1:
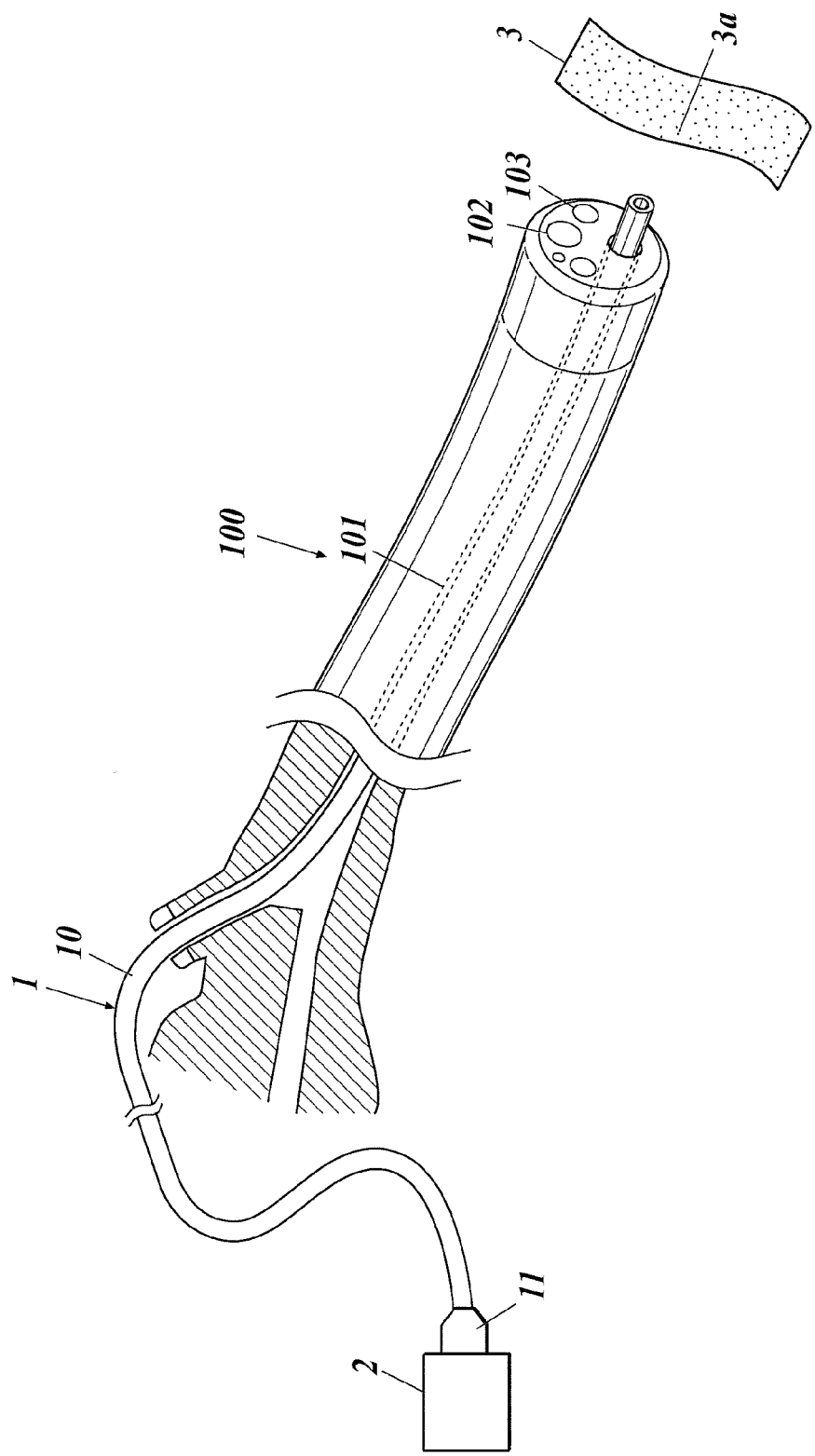
FIG. 1 is a schematic view showing usage of a probe and an endoscope according to an embodiment of the present invention.
Figure 2:
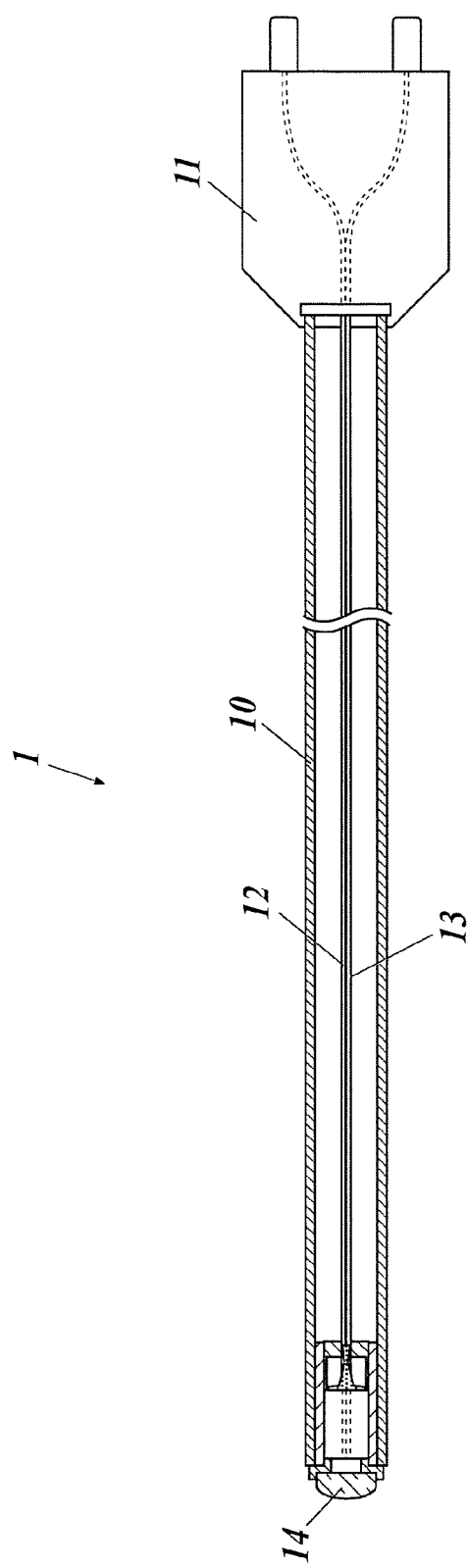
FIG. 2 is an illustration of the overall configuration of the probe according to the embodiment of the present invention.

As shown in FIG. 1, a probe 1 of the embodiments is used by being inserted into an endoscope channel 101 formed in an endoscope 100. The probe 1 is provided with a measurement optical system to irradiate a measurement target site 3a of a biological tissue 3 with irradiation light such as excitation light and receive synchrotron radiation emitted from the measurement target site 3a by the irradiation light so as to carry out measurement on the basis of the received synchrotron radiation.

The front-end face of the endoscope 101 is provided with a radiographic window 102 and an illuminating window 103. That is, the endoscope 100 has an endoscope camera to photograph inside a living body through the radiographic window 102 and an illumination device to illuminate a photography target through the illuminating window 103.

The probe 1 is inserted into the endoscope channel 101 so as to be guided to the inside of a living body and carries out optical measurement on the biological tissue 3 as a target.

The exterior of the probe 1 is constituted of a tube 10. The base end of the probe 1 is provided with an optical connecter 11 to be connected to a base unit 2.

As shown in FIGS. 2 to 4B, the probe 1 includes the tube 10, the optical connector 11, a light-emitting optical fiber 12, a light-receiving optical fiber 13, a lens 14, a cylindrical member 15, an array member 16, a fixing member 17 and an adhesive part 18. The light-emitting optical fiber 12, the light-receiving optical fiber 13, the cylindrical member 15, the array member 16, the fixing member 17 and the adhesive part 18 constitute an optical fiber assembly, and the probe 1 is configured by including this assembly.

The tube 10 has flexibility so as to guide the probe 1 to the inside of a living body through the endoscope channel 101.

The light-emitting optical fiber 12 guides the irradiation light (for example, excitation light which excites fluorescence) from a measuring light source device disposed in the base unit 2 to the front-end part of the probe 1. The measurement target site 3a of the biological tissue 3 is irradiated through the lens 14 with the irradiation light emitted from the light-emitting optical fiber 12. The synchrotron radiation (including, for example, fluorescence and reflected light generated at/by the measurement target site 3a) emitted from the measurement target site 3a by the irradiation light is condensed through the lens 14, enters the light-receiving optical fiber 13, and is guided to the base unit 2 by the light-receiving optical fiber 13.

The base unit 2 includes the measuring light source device which generates light to enter the light-emitting optical fiber 12, a light detector which detects light guided thereto by the light-emitting optical fiber 13, and a control device which controls these.

The control device of the base unit 2 controls the measuring light source device and the light detector so as to irradiate the measurement target site 3a, introduce the synchrotron radiation emitted from the measurement target site 3a into the light detector of the base unit 2, and make the light detector output the detection result.

The light detector detects light intensity, spectral characteristics, polarization characteristics and the like of the light input thereinto though the light-receiving optical fiber 13, and outputs the detection result to a measurement arithmetic unit of the control device. The measurement arithmetic unit of the control device analyzes the detection result so as to specify information useful for diagnosis of the condition of a lesion of the biological tissue 3.

In the case where the measurement with the probe 1 is measurement of fluorescence emitted from a biological tissue, the measuring light source device generates excitation light.

Fluorescence is generated by excitation light at the measurement target site 3a, which is irradiated with the excitation light, according to the condition of a lesion therein. When fluorescence is generated, the synchrotron radiation from the measurement target site 3a, the synchrotron radiation including the fluorescence and reflected light, enters the light-receiving optical fiber and is input into the light detector.

Fluorescence is, in a broad sense, excessive energy released as electromagnetic waves by an irradiated matter, which is irradiated with an X ray, an ultraviolet ray or a visible light, when electrons excited by the irradiated matter having absorbed energy of the ray/light return to the ground state. By the excitation light, fluorescence having a wavelength different from that of the excitation light is included in the optical feedback, so that the light detector separates the optical feedback into its spectral components, and the measurement arithmetic unit analyzes the spectrum distribution, thereby specifying the amount of fluorescence and detecting the condition of a lesion of a detection target.

The optical fibers 12 and 13 are core wires each formed in such a way that a bare wire constituted of a core and a clad is coated with polyimide as a primary coating. These optical fibers 12 and 13 each have a very small diameter of, for example, 0.05 to 0.5 mm, thereby having a structure which is easily damaged even by a small flaw.

Figure 4A:
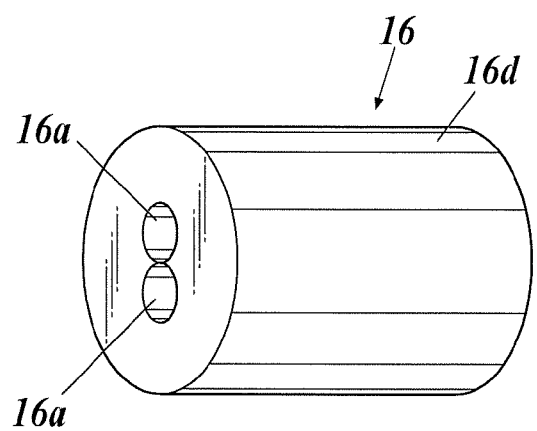
FIG. 4A is a perspective view of an array member according to the embodiment of the present invention.
Figure 4B:
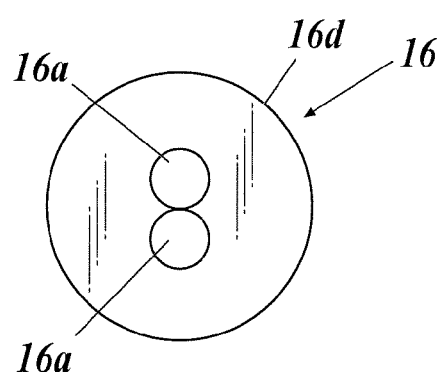
FIG. 4B is an end view of the array member according to the embodiment of the present invention.

The array member 16 is, as shown in FIGS. 4A and 4B, a microcapillary member having two through holes 16a and 16a at the center of a columnar block. The inner diameters of the through holes 16a and 16a are designed to be diameters with very small clearances added to the outer diameters of the optical fibers 12 and 13. Hence optical axes of the optical fibers 12 and 13 are adjusted with a predetermined arrangement and retained in this state by insertion of the optical fibers 12 and 13 into the through holes 16a and 16a. The array member 16 can be configured by sinter molding using zirconia, quartz glass or titanium alloy as a material.

Figure 3:
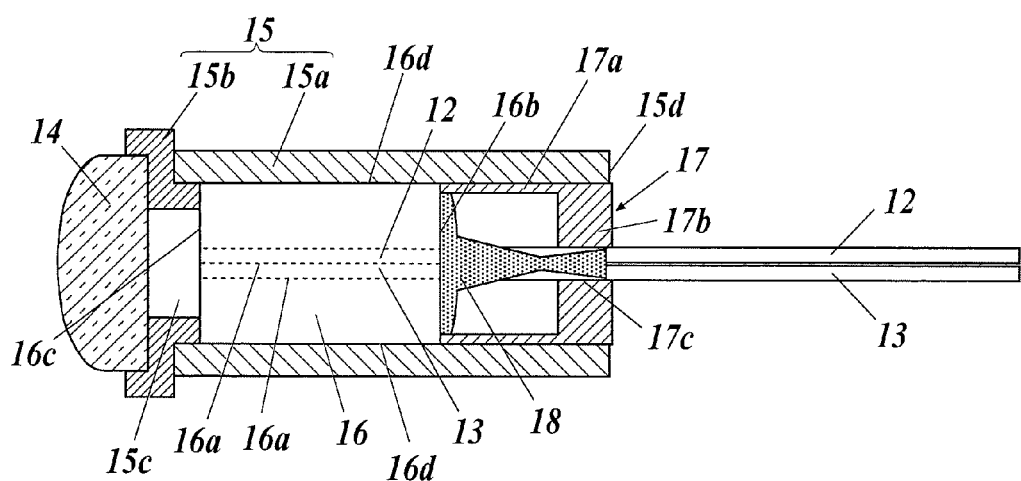
FIG. 3 is an illustration of the configuration of the front-end part of the probe according to the embodiment of the present invention.

As shown in FIG. 3, one end of the array member 16, the one end through which the two optical fibers 12 and 13 extend, is a rear end 16b, and the adhesive part 18 is disposed on the rear end 16b side. The adhesive part 18 is formed of an adhesive having curability and partly penetrates into the through holes 16a and 16a, so that the array member 16 and the optical fibers 12 and 13 adhere to each other. The adhesive which forms the adhesive part 18 is not particularly limited, but a thermosetting adhesive is mainly used. Compared with a two-liquid-mixed adhesive, use of a thermosetting adhesive has an effect of not causing inconvenience such as variation in curing characteristics by an error in a mixing ratio of a solution and hence being capable of suitably controlling time from when the adhesive is applied to when the adhesive is cured. Further, compared with an ultraviolet curable adhesive, use of a thermosetting adhesive has an effect of being capable of curing itself for sure even at a point which an ultraviolet ray is difficult to reach, such as the inner face of the through hole 16a.

The front-end faces of the two optical fibers 12 and 13 are aligned with the front end 16c of the array member 16.

Figure 5:
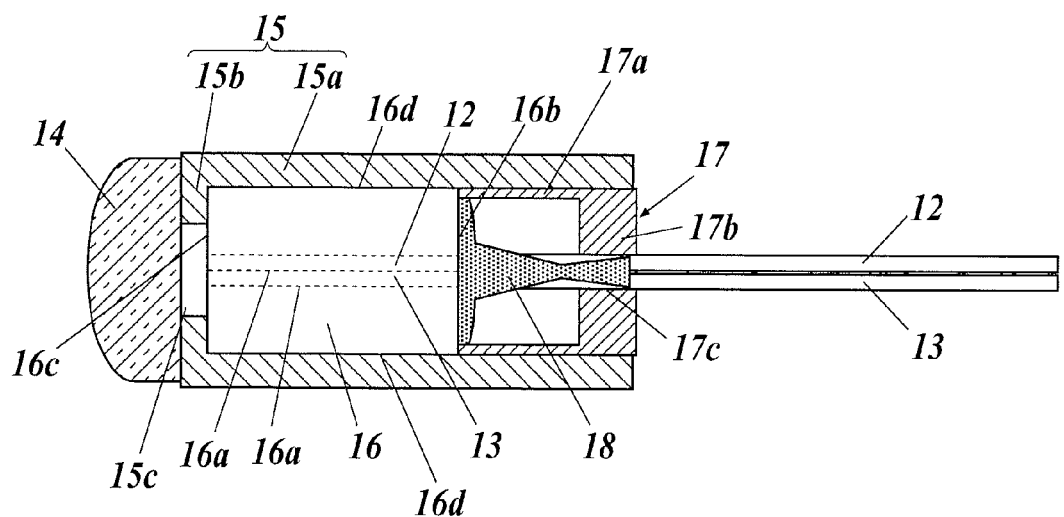
FIG. 5 is an illustration of the configuration of the front-end part of the probe according to another embodiment of the present invention.

The cylindrical member 15 is constituted of a cylindrical part 15a and a terminal part 15b. The cylindrical member 15 may be constituted of the cylindrical part 15a and the terminal part 15b which are individual components as shown in FIG. 3 or may be constituted of the cylindrical part 15a and the terminal part 15b which are integrated as one component as shown in FIG. 5. The array member 16 is inserted into the cylindrical part 15a, and the front end 16c of the array member 16 contacts the terminal part 15b so as to be fixed thereto. To the outer face of the terminal part 15b, the lens 14 is fixed. As shown in FIG. 3, the outer face of the cylindrical part 15a may be formed in a shape to retain a lens at a predetermined position. In this case, if the cylindrical part 15a and the terminal part 15b are individual components as shown in FIG. 3, the terminal part 15b may be changed to one which is fit for the shape and the size of the lens 14. The center part of the terminal part 15b is provided with a translucent hole 15c, thereby constituting an optical system capable of projecting and receiving light between the optical fibers 12 and 13 and the lens 14.

The outer circumference 16d of the array member 16 is retained by the cylindrical part 15a in such a way as to contact the inner circumference of the cylindrical part 15a. Hence, when the array member 16 is inserted into the cylindrical part 15a until the array member 16 contacts the terminal part 15b, a positional relationship of the lens 14 and the array member 16 is determined. Therefore positioning can be carried out with high accuracy.

Figure 6:
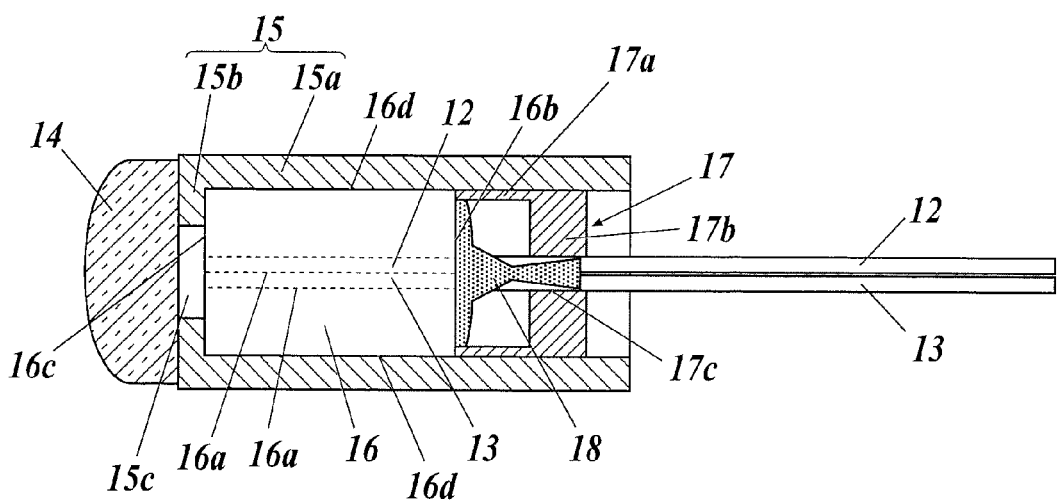
FIG. 6 is an illustration of the configuration of the front-end part of the probe according to another embodiment of the present invention.

To fix the positional relationship, the fixing member 17 is inserted into the cylindrical part 15a, following the array member 16. Hence the fixing member 17 is disposed on the rear end 16b side of the array member 16 and inserted into the cylindrical part 15a, whereby the front end of the fixing member 17 contacts the rear end 16b of the array member 16. As shown in FIGS. 3 and 5, a configuration in which the rear-end part of the fixing member 17 projects from the rear end 15d of the cylindrical part 15a in the assembling-completed state makes it easy to push the fixing member 17 to the deepest. Further, as shown in FIG. 6, a configuration in which the entire fixing member 17 is inserted into the cylindrical member 15a so that the rear end of the fixing member 17 is positioned inside the cylindrical part 15a makes the hard part shorter for a length which is resulted from the fixing member 17 not projecting from the cylindrical part 15a.

As described above, the cylindrical part 15a and the fixing member 17 are fixed to each other in the state in which: the array member 16 is sandwiched between the terminal part 15b and the fixing member 17 in the axial direction; and the array member 16 is positioned in the axial direction in relation to the cylindrical part 15a. To fix the cylindrical part 15a and the fixing member 17 to each other too, an adhesive (not shown) is used. As described above, the array member 16 and the adhesive part 18 are housed in a structure constituted of the cylindrical member 15 and the fixing member 17, so that the adhesive part 18 is protected. Therefore the optical fibers 12 and 13 can be prevented from being damaged, which occurs at the adhesive part 18 which makes the array member 16 and the optical fibers 12 and 13 adhere to each other.

The fixing member 17 includes a cylindrical part 17a and a rear-end part 17b, and the center part of the rear-end part 17b is provided with a retaining hole 17c. The retaining hole 17c is disposed a space away from the rear end 16b of the array member 16, the space where the adhesive part 18 is disposed. The retaining hole 17c is unnecessary to be formed in the rear end of the fixing member 17 and hence may be formed in a middle part of the cylindrical part 17a in the axial direction in such a way as to keep the space away from the rear end 16b. The optical fibers 12 and 13 are inserted into the retaining hole 17c, whereby the lateral faces of the optical fibers 12 and 13 are firmly attached to each other and retained therein. Thereby, as described below, the adhesive which forms the adhesive part 18 can be prevented from flowing rearward.

The procedure of a method of fabricating the above optical fiber assembly is as follows.

Step 1: First, the optical fibers 12 and 13 are inserted into the through holes 16a and 16a of the array member 16.

Thereafter, the following Steps 2 to 4 are carried out. The order of Steps 2 to 4 is not specified.

Step 2: The adhesive which forms the adhesive part 18 is applied to the rear end 16b side of the array member 16, the rear end 16b through which the optical fibers 12 and 13 extend.

Step 3: The array member 16 is inserted into the cylindrical part 15a.

Step 4: The optical fibers 12 and 13 which extend through the rear end of the array member 16 are inserted into the retaining hole 17c.

Thereafter, the following Step 5 is carried out.

Step 5: The fixing member 17 is inserted into the cylindrical part 15a in such a way that the array member 16 is sandwiched between the terminal part 15b and the fixing member 17 in the axial direction, whereby the array member 16 is positioned in the axial direction in relation to the cylindrical part 15a. Thus, they are assembled to have a positional relationship shown in FIG. 3, 5 or 6. At the time, the optical fibers 12 and 13 are firmly attached to each other and retained in the retaining hole 17c. After the adhesive to fix the fixing member 17 and the cylindrical part 15a to each other is also applied, the adhesive (s) is cured in this state.

When the adhesive is cured, the translucent hole 15c may be temporarily filled with a columnar protrusion, the length of which is adjusted to properly determine the distance from the end part of the terminal part 15b to the end parts of the optical fibers 12 and 13. There is a case where, in the process of curing the adhesive, a positional relationship of the optical fibers 12 and 13 and the array member 16 changes by stress in the curing. Then the adhesive is cured with the protrusion and the optical fibers 12 and 13 contacting each other. Therefore positioning accuracy can be made higher.

As described above, the adhesive is cured in the state in which the optical fibers 12 and 13 are firmly attached to each other and retained in the retaining hole 17c, whereby the space between the optical fibers 12 and 13 disappears at apart of the retaining hole 17c. Hence it does not happen that the adhesive runs rearward in the longitudinal direction of the optical fibers 12 and 13 by capillary phenomenon and flows out from the retaining hole 17c rearward. Therefore the adhesive can be prevented from spreading over a long area and solidifying therein, and the hard part of the front-end part of the probe, the hard part where flexibility is lost, can be made short.

The optical fiber assembly thus configured is inserted into the tube 10. The optical connector 11 is disposed on one end of the tube 10, and the cylindrical member 15 is fixed to the other end of the tube 10. Thus, the probe 1 is configured.

The probe 1 is described more specifically with numerical values as examples.

As described above, the optical fiber assembly of the embodiments is built in the probe 1 which is inserted into a human body through the endoscope channel 101, and the front-end part needs to be flexibly bendable to follow bending actions of the front-end part of an endoscope. An endoscope is configured in such a way that the front end thereof is bendable to change its direction nearly 180 degrees in the gullet of a person. To make the front-end part of the probe 1 flexibly bendable to follow this change, the part more than 10 mm away from the front end of the probe 1 needs to be a flexible part, at least. To make the length of the hard part short, as with the embodiments, it is desirable to make the length of the array member 16 shorter than the insertable length of the inside of the cylindrical member 15, the insertable length up to which the array member 16 is allowed to be inserted into the cylindrical member 15. Further, according to the embodiments, the adhesive part 18 which fixes the array member 16 and the optical fibers 12 and 13 to each other is also disposed inside the structure constituted of the cylindrical member 15 and the fixing member 17, and when the probe 1 is curved, the posterior part of the tube 10, the posterior part being the part behind the cylindrical member 15 and the fixing member 17, is curved. Hence no strong stress is generated at the adhesive part, which reduces a risk that the optical fibers 12 and 13 are damaged at the adhesive part 18.

In assembling, the fixing member 17 assists a work to send the array member 16 deep inside the cylindrical part 15a while contacting the rear end 16b of the array member 16 and the inner circumferential face of the cylindrical part 15a.

In the case where the full length of the cylindrical member 15 is 8 mm and the insertable length of the inside of the cylindrical member 15, the insertable length up to which the array member 16 is allowed to be inserted into the cylindrical member 15, is 7 mm, if the length of the array member 16 is 3 mm and the distance from the rear end 16b of the array member 16 to the rear end of the adhesive part 18 is 4 mm, the length of the hard part can be made to be the minimum and the adhesive part 18, which has high possibility of being damaged, can be protected by being placed inside, by pushing the array member 16 with the fixing member 17, thereby inserting the fixing member 17 and the array member 16 into the cylindrical member 15.

As described above, the retaining hole 17c of the fixing member 17 also functions to block, on the way, the adhesive which makes the array member 16 and the optical fibers 12 and 13 adhere to each other from flowing into the space between the optical fibers 12 and 13 by capillary phenomenon and running over a long section. The retaining hole 17c of the fixing member 17 is arranged in an area of 5 mm or less from the rear end 16b of the array member 16. With this arrangement, even when the flowing of the adhesive occurs, a predetermined length of a cured part by the flowing can be kept within that of the fixing member 17. This effect can be obtained whether the fixing member 17 projects outside the cylindrical member 15 as shown in FIGS. 3 and 5 or is inside the cylindrical member 15 as shown in FIG. 6.

Figure 7:
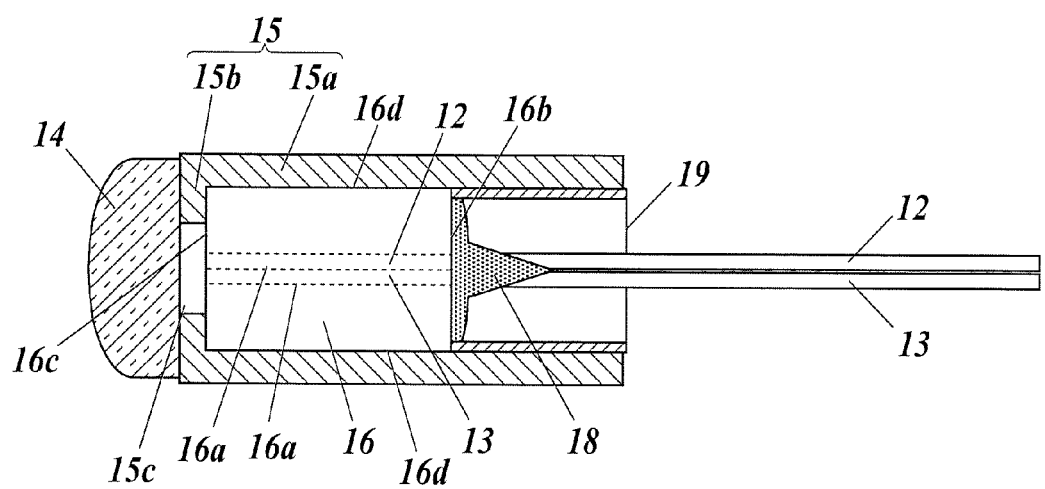
FIG. 7 is an illustration of the configuration of the front-end part of the probe according to another embodiment of the present invention.

Further, even when a fixing member 19, the rear end of which is open as shown in FIG. 7, is used with no retaining hole 17c shown in FIGS. 3, 5 and 6 formed, the adhesive part 18 can be protected by housing the adhesive part 18 in a structure constituted of the cylindrical member 15 and the fixing member 19. For example, the adhesive can be prevented from flowing rearward and the fabricating can be carried out by retaining the optical fibers 12 and 13 with a jig, thereby making the space between the optical fibers 12 and 13 disappear near the array member 16, as with the case of using the retaining hole 17c.

In the above embodiments, the optical fibers emit excitation light to a measurement target site and receive, as an example, fluorescence generated by the excitation light, but may receive scattered light or Raman scattered light generated by irradiation light. In these cases too, diagnosis can be made on degeneration of a biological tissue or the condition of a disease such as a cancer.

Further, in the above embodiments, the number of optical fibers provided in the probe and retained by the array member is two, but may be three or more. The effect described above can be obtained with three or more optical fibers too. The light-emitting optical fiber 12 can be configured with either one optical fiber or a plurality of optical fibers. The light-receiving optical fiber 13 can also be configured with either one optical fiber or a plurality of optical fibers. The light-emitting optical fiber and the light-receiving optical fiber can be configured with a plurality of optical fibers in total.

INDUSTRIAL APPLICABILITY

The present invention is applicable to transmission of light received from an examination target or the like.

EXPLANATION OF REFERENCE NUMERALS

1 Probe
2 Base Unit
3 Biological Tissue
10 Tube
11 Optical Connector
12 Light-Emitting Optical Fiber
13 Light-Receiving Optical Fiber
14 Lens
15 Cylindrical Member
15a Cylindrical Part
15b Terminal Part
15c Translucent Hole
15d Rear End
16 Array Member
16a Through Hole
16b Rear End
16c Front End
16d Outer Circumference
17 Fixing Member
17a Cylindrical Part
17b Rear-End Part
17c Retaining Hole
18 Adhesive Part
19 Fixing Member
100 Endoscope
101 Endoscope Channel

The invention claimed is:

1. An optical fiber assembly comprising:
a plurality of optical fibers;
an array member into which the optical fibers are inserted and which retains the optical fibers with a predetermined arrangement;
an adhesive part which (i) is disposed on a one-end side where one end of the array member is disposed, the one end through which the optical fibers extend, (ii) is formed of an adhesive having curability and (iii) makes the array member and the optical fibers adhere to each other;
a structure comprising of a cylindrical member and a fixing member;
the cylindrical member including:
  a cylindrical part into which the array member is inserted and which retains an outer circumference of the array member; and
  a terminal part which contacts another end of the array member; and
the fixing member which (i) is disposed on the one-end side of the array member, (ii) is entirely or partly inserted into the cylindrical part and (iii) contacts the one end of the array member,
wherein the cylindrical part and the fixing member are fixed to each other in a state in which (i) the array member is sandwiched between the terminal part and the fixing member in an axial direction and (ii) the array member is positioned in the axial direction in relation to the cylindrical part, whereby the array member and the adhesive part are housed in the structure constituted of the cylindrical member and the fixing member, and
wherein the outer circumference of the array member is retained by the cylindrical part in such a way as to contact a inner circumference of the cylindrical part.

2. The optical fiber assembly according to claim 1, wherein the cylindrical member is constituted of the terminal part and the cylindrical part which are individual components.

3. The optical fiber assembly according to claim 1, wherein the cylindrical member is constituted of the terminal part and the cylindrical part which are integrated as a component.

4. The optical fiber assembly according to claim 1,
wherein the fixing member is provided with a retaining hole into which the optical fibers are inserted,
wherein the retaining hole extends away from the one end of the array member and through the adhesive part, and
wherein the optical fibers are firmly attached to each other and retained in the retaining hole by the adhesive part.

5. A probe comprising:
the optical fiber assembly according to claim 1;
a tube into which the optical fiber assembly is inserted; and
an optical connector which is disposed on one end of the tube and connects the optical fibers to an optical device,
wherein the cylindrical member is fixed to another end of the tube.

6. A method of fabricating an optical fiber assembly comprising:
a plurality of optical fibers;
an array member into which the optical fibers are inserted and which retains the optical fibers with a predetermined arrangement;
an adhesive part which (i) is disposed on a one-end side where one end of the array member is disposed, the one end through which the optical fibers extend, (ii) is formed of an adhesive having curability and (iii) makes the array member and the optical fibers adhere to each other;
a structure comprising of a cylindrical member and a fixing member;
the cylindrical member including:
  a cylindrical part into which the array member is inserted and which retains an outer circumference of the array member; and
  a terminal part which contacts another end of the array member; and
the fixing member which (i) is disposed on the one-end side of the array member, (ii) is entirely or partly inserted into the cylindrical part and (iii) contacts the one end of the array member,
wherein the cylindrical part and the fixing member are fixed to each other in a state in which (i) the array member is sandwiched between the terminal part and the fixing member in an axial direction and (ii) the array member is positioned in the axial direction in relation to the cylindrical part, whereby the array member and the adhesive part are housed in the structure constituted of the cylindrical member and the fixing member,
wherein the outer circumference of the array member is retained by the cylindrical part in such a way as to contact a inner circumference of the cylindrical part,
wherein the fixing member is provided with a retaining hole into which the optical fibers are inserted,
wherein the retaining hole extends away from the one end of the array member and through the adhesive part, and
wherein the optical fibers are firmly attached to each other and retained in the retaining hole by the adhesive part, the method comprising:

inserting the optical fibers into the array member;

applying the adhesive which forms the adhesive part to the one-end side where the one end of the array member is disposed, the one end through which the optical fibers extend;

inserting the array member into the cylindrical part;

inserting the optical fibers which extend through the one end of the array member into the retaining hole; and thereafter;

inserting the fixing member into the cylindrical part in such a way as to sandwich the array member between the terminal part and the fixing member in the axial direction, thereby positioning the array member in the axial direction in relation to the cylindrical part; and curing the adhesive in a state in which the optical fibers are firmly attached to each other and retained in the retaining hole.

* * * * *